United States Patent [19]

Ostermaier et al.

[11] Patent Number: 5,892,122

[45] Date of Patent: Apr. 6, 1999

[54] METHOD FOR MAKING CYCLOHEXANOL AND CYCLOHEXANONE

[75] Inventors: John Joseph Ostermaier, Wilmington, Del.; George Crumbaugh Russell, III, Orange, Tex.

[73] Assignee: E. I. du Pont de Nemours and Company, Wilmington, Del.

[21] Appl. No.: 918,779

[22] Filed: Aug. 25, 1997

[51] Int. Cl.$^6$ .............................. C07C 35/08; C07C 45/32
[52] U.S. Cl. ............................ 568/357; 568/358; 568/836
[58] Field of Search ..................................... 568/357, 358, 568/836

[56] References Cited

U.S. PATENT DOCUMENTS 5,126,505   6/1992   Chang .

*Primary Examiner*—Johann Richter
*Assistant Examiner*—Taofiq A. Solola

[57] ABSTRACT

An improved method for making cyclohexanone and cyclohexanol from oxidation of cyclohexane in which a polyprotic acid is used to neutralize caustic to prevent oligomerization of cyclohexanone during fractional distillation.

4 Claims, No Drawings

METHOD FOR MAKING CYCLOHEXANOL AND CYCLOHEXANONE

BACKGROUND OF THE INVENTION

The first step in the manufacture of adipic acid and caprolactam is oxidizing cyclohexane to produce a mixture containing unreacted cyclohexane, cyclohexanone, cyclohexanol and cyclohexylhydroperoxide (CHHP), and treating the mixture with aqueous caustic to decompose the CHHP into more cyclohexanone and cyclohexanol. The treatment results in a biphasic mixture: an organic phase, containing primarily cyclohexane, cyclohexanone and cyclohexanol, and an aqueous phase containing primarily water, organic salts and caustic. However, inevitably some caustic tends to remain in the organic phase in the form of dispersed droplets. Isolation of the cyclohexanone and cyclohexanol is accomplished typically by fractional distillation, in which the cyclohexanone is exposed to heat. In commercial operations, fractional distillation is conducted in metallic stills which frequently are made from metals which are susceptible to corrosion when contacted by acidic media. Even a small amount of caustic present during this fractional distillation step can catalyze the oligomerization of some of the cyclohexanone, resulting in yield loss. Moreover if the cyclohexanone/cyclohexanol mixture is converted to adipic acid, the presence of cyclohexanone oligomers can cause fouling of equipment and contamination of adipic acid. It would be desirable to have a way of limiting the extent of cyclohexanone oligomerization in the processes described above.

SUMMARY OF THE INVENTION

The object of the present invention is to provide a method for limiting the amount of cyclohexanone oligomerization in the above-described process without creating acidic conditions which can cause corrosion of metallic fractional distillation stills and other equipment. The present invention is an improved process for making cyclohexanol and cyclohexanone by air oxidation of cyclohexane. The unimproved process comprises the steps of:

(1) reacting cyclohexane with air to produce a first mixture comprising cyclohexanol, cyclohexanone, cyclohexylhydroperoxide and cyclohexane;

(2) reacting the cyclohexylhydroperoxide with aqueous caustic and optionally a cobalt catalyst to produce a second mixture comprising an organic phase comprising cyclohexanol, cyclohexanone and cyclohexane and an aqueous phase comprising water and caustic;

(3) separating the aqueous phase of the second mixture from the organic phase of the second mixture;

(4) contacting the organic phase with water to extract a portion of the caustic contained therein;

(5) distilling the organic phase to separate the cyclohexane from the cyclohexanol and cyclohexanone.

The improvement comprises including in the water in step (4) at least one polyprotic acid capable of neutralizing the caustic and forming a buffer whose pH is in the range of 7.0 to 9.5, whereby oligomerization of cyclohexanone in step (5) is substantially eliminated.

DETAILED DESCRIPTION OF THE INVENTION

In a typical commercial process to make adipic acid or caprolactam, cyclohexane is reacted in an air oxidizer with oxygen to produce a mixture containing unreacted cyclohexane, cyclohexanone, cyclohexanol, and cyclohexylhydroperoxide (CHHP). The mixture is then transferred to a CHHP decomposition reactor where it is treated with aqueous caustic, generally NaOH, and optionally a cobalt catalyst. As a result of this treatment, a biphasic mixture is produced. One phase is organic and contains cyclohexane, cyclohexanone, and cyclohexanol, as well as some entrapped aqueous caustic which can impart turbidity to this phase. The other phase is aqueous and contains water, most of the caustic and minor amounts of salts of organic acids, e.g., adipates, glutarates, etc. The organic phase is separated from the aqueous phase using at least one decantation, which removes the aqueous phase as a waste stream.

The organic phase is then mixed in a second decanter with fresh water which includes a polyprotic acid, forming a solution whose pH is buffered in the pH range of about 7.0 to about 9.5, more preferably about 8.0 to 9.5.

Suitable polyprotic acids are generally tri or diprotic acids such as carbonic acid and phosphoric acid. Carbonic acid is preferred. Conveniently, the carbonic acid can be made by contacting $CO_2$ with the fresh water as the water is being introduced into the second decanter. The use of polyprotic acids offers the advantage of being able to neutralize the caustic without the danger of making the organic phase too acidic, which can lead to corrosion problems in downstream equipment. After mixing, the resulting organic and aqueous phases are separated, and the aqueous phase, containing some neutralized caustic, can be discarded or appropriately recycled.

After the aqueous and organic phases of the second decanter are separated, further buffered water washes and decantations can be performed, reducing further any caustic contained in the mixture of cyclohexane, cyclohexanone and cyclohexanol.

Finally, the mixture of cyclohexane, cyclohexanone and cyclohexanol can be separated in stills by fractional distillation to recover substantially pure cyclohexanone and cyclohexanol with little or no formation of cyclohexanone oligomers. Cyclohexane can be returned to the initial air oxidizer for further reaction.

The present invention is illustrated by the following nonlimiting examples.

The examples below are based on experiments which were performed by placing 45% cyclohexanone (K) and 55% nonane in a refluxing batch reactor equipped with a Dean Stark trap to continuously remove water. This reaction mixture refluxes at 145 degrees C. To this mixture was added various chemicals to determine their effectiveness to catalyze formation of K dimer. Chemicals tested were NaHCO3, Na2CO3, and NaOH. As the mixture was heating up to normal reflux, the water was removed by the Dean Stark trap, and the chemicals were converted to a separate solid phase. In addition, experiments were run where $CO_2$ was sparged through mixtures containing NaOH prior to stripping off the water in order to neutralize the NaOH. Samples of the reactor contents were taken at various intervals and analyzed for dimers and trimers of K.

COMPARATIVE EXAMPLE (Dependence of Dimer Formation on Catalyst Type)

Experiments were run where 1200 ppm Na was added as $NaHCO_3$, $Na_2CO_3$, and NaOH. In addition, a blank was run where no sodium-containing compound was added. Concentrations of dimer are shown as a function of time in Table

1.

TABLE 1

| t (hrs) | Blank | NaHCO$_3$ | ppm Dimer Na$_2$CO$_3$ | NaOH |
|---|---|---|---|---|
| 0.5 | — | — | — | 110,000 |
| 1.0 | 20 | 37 | 50 | 216,000 |
| 2.0 | 50 | 110 | 100 | — |
| 4.0 | 110 | 280 | 260 | — |

These data clearly show that caustic is an undesirably highly active catalyst for dimer formation, and that sodium bicarbonate and carbonate are very weak catalysts, if at all. These results suggest that reacting caustic with $CO_2$ to convert it to the carbonate and bicarbonate forms can greatly suppress dimer formation in the step where K and A are separated from unreacted cyclohexane by distillation.

Example 1

(Addition of $CO_2$ to Suppress Dimer Formation)

An experiment was run to verify the efficacy of $CO_2$ for neutralization of caustic and suppression of dimer formation. In this case, 1200 ppm Na as NaOH was added to the reaction mixture, together with a trace of thymolphthalein indicator solution, and then $CO_2$ was bubbled through the reactor until the indicator changed from blue to colorless. This corresponds to about half of the caustic being neutralized to bicarbonate, and half to carbonate. The reactor was then heated, and dimer formation as a function of time was determined. The results are shown in Table 2, which show the effect of $CO_2$ on suppression of dimer formation (1200 ppm Na).

TABLE 2

| t (hrs) | Blank | ppm Dimer $CO_2$ Added | NaOH |
|---|---|---|---|
| 0.5 | — | 20 | 110,000 |
| 1.0 | 20 | 60 | 216,000 |
| 2.0 | 50 | 130 | — |

Example 2

(Effect of $CO_2$ on Suppression of Dimer Formation (240 ppm Na))

Example 2 was run like Example 1 except that the experiments were performed at a lower sodium concentration of 240 ppm Na as NaOH. These results are presented in Table 3, which shows the effect of $CO_2$ on suppression of dimer formation (240 ppm Na).

TABLE 3

| t (hrs) | Blank | ppm Dimer $CO_2$ Added | NaOH |
|---|---|---|---|
| 0.5 | — | 20 | 1290 |
| 1.0 | 20 | 40 | 5290 |
| 2.0 | 50 | 110 | 14,100 |

These results again show the ability of $CO_2$ to suppress dimer formation. Comparison of the data in Tables 2 and 3 indicates that the rate of dimer formation is greatly reduced by reducing the caustic concentration.

What is claimed is:

1. In a process for making cyclohexanol and cyclohexanone by air oxidation of cyclohexane, which comprises the steps of:

(1) reacting cyclohexane with air to produce a first mixture comprising cyclohexanol, cyclohexanone, cyclohexylhydroperoxide and cyclohexane;

(2) reacting the cyclohexylhydroperoxide with aqueous caustic and optionally a cobalt catalyst to produce a second mixture comprising an organic phase comprising cyclohexanol, cyclohexanone and cyclohexane and an aqueous phase comprising water and caustic;

(3) separating the aqueous phase of the second mixture from the organic phase of the second mixture;

(4) contacting the organic phase with water to extract a portion of the caustic contained therein;

(5) distilling the organic phase to separate the cyclohexane from the cyclohexanol and cyclohexanone;

the improvement comprising including in the water in step 4 at least one polyprotic acid capable of neutralizing the caustic and forming a buffer whose pH is in the range of 7.0 to 9.5, whereby oligomerization of cyclohexanone in step (5) is substantially eliminated.

2. The process of claim 1 wherein the pH range is 8.0 to 9.5.

3. The process of claim 1 wherein the polyprotic acid is carbonic acid.

4. The process of claim 3 wherein the carbonic acid is formed by contacting the water in step (4) with carbon dioxide.

* * * * *